(12) United States Patent
Sullivan et al.

(10) Patent No.: US 7,169,607 B2
(45) Date of Patent: *Jan. 30, 2007

(54) IN VIVO INDUCTION FOR ENHANCED FUNCTION OF ISOLATED HEPATOCYTES

(75) Inventors: Susan J. Sullivan, Newton, MA (US); Paul G. Gregory, Shrewsbury, MA (US); Paul A. DiMilla, Dover, MA (US)

(73) Assignee: Organogenesis, Inc, Canton, MA (US)

( * ) Notice: Subject to any disclaimer, the term of this patent is extended or adjusted under 35 U.S.C. 154(b) by 373 days.

This patent is subject to a terminal disclaimer.

(21) Appl. No.: 10/607,695

(22) Filed: Jun. 27, 2003

(65) Prior Publication Data

US 2004/0005303 A1  Jan. 8, 2004

Related U.S. Application Data

(62) Division of application No. 10/036,593, filed on Dec. 21, 2001, now Pat. No. 6,699,716, which is a division of application No. 09/621,921, filed on Jul. 24, 2000, now Pat. No. 6,394,812.

(60) Provisional application No. 60/145,362, filed on Jul. 22, 1999.

(51) Int. Cl.
*C12N 5/00* (2006.01)

(52) U.S. Cl. ............... 435/375; 424/93.7; 435/289.1

(58) Field of Classification Search ............ 435/375, 435/289.1; 424/93.7

See application file for complete search history.

(56) References Cited

U.S. PATENT DOCUMENTS

| | | | |
|---|---|---|---|
| 5,030,105 A | 7/1991 | Kuri-Harcuch et al. | |
| 5,445,956 A | 8/1995 | Hammock et al. | |
| 5,466,696 A | 11/1995 | Woolf | |
| 5,506,131 A | 4/1996 | Harris et al. | |
| 5,576,207 A | 11/1996 | Reid et al. | |
| 5,602,026 A | 2/1997 | Dunn et al. | |
| 5,658,797 A | 8/1997 | Bader | |
| 5,866,420 A | 2/1999 | Talbot et al. | |
| 5,869,243 A | 2/1999 | Jauregui et al. | |
| 5,942,436 A | 8/1999 | Dunn et al. | |
| 6,127,117 A | 10/2000 | Morris et al. | |
| 6,394,812 B1 * | 5/2002 | Sullivan et al. | 434/375 |
| 6,699,716 B2 * | 3/2004 | Sullivan et al. | 435/375 |

FOREIGN PATENT DOCUMENTS

WO  96/34087  10/1996

OTHER PUBLICATIONS

Asaka et al., "Localization of xenobiotic responsive element binding protein in rat hepatocyte nuclei after methylcholanthrene administration as revealed by in situ southwestern hybridization," J. of Histochem. & Cytochem., vol. 46, No. 7, pp. 825-832 (1998).

Baron et al. Effects of 3-methylcholanthrene, β-naphthoflavone and phenobarbital on the 3-methylcholanthrene-inducible isozyme of cytochrome p-450 within centrilobular, midzonal and periportal hepatocytes (1982) J. Biol. Chem., vol. 257, No. 2, pp. 953-957.

Bhatia, S.N. et al., "Microfabrication of Hepatocyte/Fibroblast co-cultures: Role of Homotypic cell interactions," Biotechnol. Prog., vol. 14, pp. 378-387 (1998).

Bhatia, S.N. et al., "Effect of cell-cell interactions in preservation of cellular phenotype: cocultivation of hepatocytes and nonparenchymal cells," FASEB, vol. 13, pp. 1883-1900 (1999).

Cottrell et al., "Strain specific enhancement or inhibition of coumarin hepatoxicity in mince following pretreatment with two different liver enzyme inducing agents," Fundamental and Applied Toxicology, vol. 34, pp. 47-55 (1996).

Jauregui, H.O. et al, "Xenobiotic induction of P-450 PB-4 (IIB1) and P-450-c (IA1) and associated monooxygenase activities in primary cultures of adult rat hepatocytes," Xenobiotica, vol. 21, No. 9, pp. 1091-1106 (1991).

Jones, E.A. et al., "Hepatic encephalopathy and benzodiazepine receptor ligands," in *Hepatic Encephalopathy: Pathophysiology and Treatment* (Butterworth and Layrargues eds.) Humana Press (Clifton, NJ) pp. 273-286 (1989).

Monshouwer et al., Characterization of cytochrome p450 isoenzymes in primary cultures of pig hepatocytes (Dec. 1998) Toxicology in Vitro, vol. 12, pp. 715-723.

Morel et al. Prefernital increase of glutathione s-transferase class α transcripts in cultured human hepatocytes by phenobarbital, 3-methylcholanthrene, and dithiolethiones (1993) Cancer Research, vol. 53, pp. 231-234.

Naik, S. et al, "Isolation and culture of porcine hepatocytes for artificial liver support," Cell Transplantation, vol. 5, No. 1, pp. 107-115 (1996).

Nishibe, Y. et al., "Induction of cytochrome P-450 isoenzymes in cultured monkey hepatocytes," Int. J. Biochem. Cell Biol., vol. 27, No. 3, pp. 279-285 (1995).

Nishibe et al., Effects of phenobarbital and other model inducers on cytochrome p450 isozymes in primary culture of dog hepatocytes (1993) Xenobiotica, vol. 23, No. 6, pp. 681-692.

Nyberg, S. et al., "Pharmacokinetic analysis verifies P450 function during in vitro and in vivo application of a bioartificial liver," ASAIO Journal, pp. M252-M256 (1993).

(Continued)

*Primary Examiner*—Leon Blaine Lankford, Jr.
(74) *Attorney, Agent, or Firm*—Kramer Levin Naftalis & Frankel (57) ABSTRACT

The invention features a liver cell culture comprising hepatocytes that have increased detoxification enzyme activity when isolated from a liver of a donor that had been administered at least one induction agent prior isolation of hepatocyte cells. The induced hepatocytes are used in a bioreactor and cultured to produce hepatocyte cell products or metabolize toxins added to the culture. The bioreactor is, or is an integral part of, a liver assist device used to treat a patient in need of liver assist.

13 Claims, 4 Drawing Sheets

OTHER PUBLICATIONS

Oinonen et al., "Pretranslational induction of cytochrome P4501 A enzymes by β-napthoflavone and 3-methylcholanthrene occurs in different liver zones," Biochemical Pharmacology, vol. 48, No. 12, pp. 2189-2197.

Seglen, P.O., "Preparation of isolated rat liver cells," in *Methods in Cell Biology*, (DM Prescott ed.) vol. 13, Academic Press (NY, NY) pp. 29-83 (1976).

Silva et al., "Induction of cytochrome-p450 in cryopreserved rat and human hepatocytes," Chemico-Biological Interactions, vol. 121, pp. 49-63 (1999).

Thomas, P.E. et al., "Induction of two immunochemically related rat liver cytochrome P-450 isozymes, cytochromes P-450c and P-450d, by structurally diverse xenobiotics," Journal of Biological Chemistry, vol. 258, No. 7, pp. 4590-4598 (1983).

van't Klooster et al., Cytochrome p450 induction and metabolism of alkoxyresorufins, ethylmorphine and testosterone in cultured hepatocytes from goats, sheep and cattle (1993) Biochemical Pharmacology, vol. 46, No. 10, pp. 1781-1790.

Donato et al., Abstract: "Effect of Model Inducers on Cytochrome P450 Activities of Human Hepatocytes in Primary Culture," Database Medline Online, US National Library of Medicine (NLM), Database Accession No. NLM7587930, May 1995.

Gomez-Lechon et al., "Long-term Expression of Differentiated Functions in Hepatocytes Cultured in Three-Dimensional Collagen Matrix," Journal of Cellular Physiology, Dec. 1998, vol. 177, No. 4, pp. 553-562.

\* cited by examiner

IN VIVO INDUCTION FOR ENHANCED FUNCTION OF ISOLATED HEPATOCYTES

CROSS-REFERENCE TO RELATED APPLICATIONS

This is a divisional of U.S. application Ser. No. 10/036,593, filed Dec. 21, 2001, now U.S. Pat. No. 6,699,716, issued Mar. 2, 2004, which is a divisional of U.S. application Ser. No. 09/621,921, filed Jul. 24, 2000, now U.S. Pat. No. 6,394,812, issued May 28, 2002, which claims the benefit to and priority of U.S. Provisional Application Ser. No. 60/145,362, filed Jul. 22, 1999, all of which are hereby incorporated by reference in their entirety.

1. Field of the Invention

The field of the invention is cell culture and medical biotechnology, particularly hepatocyte cell cultures used in liver assist devices for treating a patient with liver disease. Hepatocyte cells are induced in vivo, procured from the liver organ, cultured and incorporated in a device to treat a patient via the bloodstream to provide hepatic function. The hepatocyte isolation methods of the invention provide enhanced cell function that extends the functionality of the cells in the course of treating the patient.

2. Background of the Invention

Extracorporeal liver assist devices (LAD) have been proposed as a treatment for patients in acute or fulminant liver failure. The LAD would function as a temporary support designed to provide hepatic function until liver transplantation or the regeneration of the patient's own liver. The LAD incorporates a bioreactor containing isolated porcine hepatocytes that are expected to detoxify substances in the circulating plasma of patients in liver failure. However, one of the challenges in using isolated hepatocytes is that many of these differentiated activities are transient, lasting only hours to a few days in culture (Nishibe, Y, and Hirata, M. *Induction of cytochrome P-450 isozymes in cultured monkey hepatocytes.* Int J Biochem Cell Bio. 27:3:279–285. 1995. Jauregui, H O, Ng, S F, Gann, K L and Waxman, D J. *Xenobiotic induction of P-450 PB-4 (IIB1) and P-450c (IA1) and associated monooxygenase activities in primary cultures of adult rat hepatocytes.* Xeno, 21(9):1091–106. 1991. Niak, S, Trenkler, D, Santangini, H, Pan, J and Jauregui, H O. *Isolation and culture of porcine hepatocyte for artificial liver support.* Cell Trans 5:107–115, 1996.) These functional detoxification activities exist as a family of enzymes, including cytochrome P450 isoenzymes, with each enzyme responsible for metabolism of specific substrates.

While the roles of hepatocytes in a LAD are multifold, one of their most critical functions is detoxification mediated by detoxification enzymes. Therefore, the maintenance of P450 cytochrome and other detoxification activity of hepatocyte cultures is of interest in the successful treatment of fulminant hepatic failure with a liver assist device.

The method of the invention increases enzyme activity in normal hepatocytes as much as 100-fold or more and that enhanced activity is maintained for at least one week in culture. This sustained level of detoxification activity from in vivo induction methods is significantly higher than levels found in non-induced hepatocytes or those obtained using in vitro induction methods. The cells maintain this level of function when incorporated in bioreactor culture to produce cell products and metabolize toxic substances. The invention described here would serve the medical community by increasing the detoxification capabilities of hepatocytes to be used therapeutically when the bioreactor is used as, or incorporated into, a liver assist device.

SUMMARY OF THE INVENTION

The invention features a liver cell culture comprising hepatocytes that have increased functional enzyme activity when isolated from a liver of a donor that had been administered at least one induction agent in vivo prior to isolation of hepatocyte cells from the liver. The induced hepatocytes are used in a bioreactor and cultured to produce hepatocyte cell products or metabolize toxins added to the culture, or both. In the preferred embodiment, the bioreactor is, or is an integral part of, a liver assist device used to treat a patient in need of liver assist. In another preferred embodiment at least two cultures of hepatocytes from different isolations induced by different induction agents may be mixed or used together in a bioreactor to have a bioreactor that exhibits a wider range of increased functional enzyme activity.

DESCRIPTION OF THE FIGURES

FIG. 1 presents the effects of phenobarbital on in vitro and in vivo induced hepatocytes. In vitro induction of CYPIIB2 (BROD), FIG. 1a, and CYPIIB1 (PROD), FIG. 1b, with phenobarbital (PB) is shown. In vivo induction of CYPIIB2 (BROD), FIG. 1c, and CYPIB1 (PROD), FIG. 1d, is also shown.

FIG. 3 depicts the effects of 3-methylcholanthrene ("3 MC" or "MC") on both in vitro and in vivo induced hepatocyte cultures. In vitro induction of CYPIA2 (MROD) is shown in FIG. 3a, and CYPIA1 (EROD) in FIG. 3b.

DETAILED DESCRIPTION OF THE INVENTION

Heretofore, cell cultures from liver procured from induced donors have not been incorporated in a bioreactor, particularly for use in a liver assist device.

In the method to obtain induced cells, a liver donor is selected and screened for appropriate age and health necessary to obtain healthy cells from the donor's organs. The liver donor for obtaining hepatocytes is preferably a normal or transgenic animal donor of either mammalian or rodent species, more preferably of equine, canine, porcine, bovine, ovine, or murine species; and most preferably, a porcine donor. Due to the ease of handling smaller animals and liver organs, pigs between about 5 kg to about 20 kg are used, preferably about 8 kg, but any size donor may be used as a source for liver organs.

Induction is preferably performed by administering at least one induction agent to an animal donor via direct injection to the bloodstream, intraperitoneally, or intramuscularly; however, induction agents may also be administered to a donor using other routes such as orally, transdermally, or by inhalation. One or more agents may be administered at one time in a single dose or over a time as separated doses of different induction agents. The donor may be dosed with a combination of two or more induction agents to upregulate certain desired detoxification enzymes to create a hepatocyte culture having a customized enzyme activity profile. The dosing of the induction agent may be administered in a single day or over a time, such as over a number of hours or days, before isolating the hepatocyte cells from the donor liver. For example, some induction agents such as phenobarbital are relatively unstable molecules after injection to a donor and are, therefore, more effective if provided at multiple intervals prior to procuring the organ. The amount of the induction agent in the dose depends on (1) the induction agent or agents used, (2) the species, sex, and size of the donor, (3) the mode of administration of at least one induction agent, and (4) the frequency of dose administration. Typically, when the induction agent is administered over a series of doses, the dosage of induction agent may be less. One of skill in the art would be able to successfully determine how to manipulate these dosing parameters in order to obtain in vivo induced hepatocyte cultures for use in the method and bioreactor of the invention.

"Induction agent" means an agent that is capable of increasing or upregulating hepatocyte cell functions, particularly those enzymes involved with detoxification, particularly cytochrome P450 or the conjugative reactions involved in detoxification. It is also useful if the induction agent maintains or improves other hepatocyte cell functions including metabolic functions such as ammonia clearance and synthetic functions such as albumin and transferrin production.

Induction agents are selected from the group including but not limited to: beta-naphthoflavone (BNF), phenobarbital, 3-methylcholanthrene (3MC), ethanol, dexamethasone, arochlor 1254, 2,3,7,8-tetrachlorodibenzo-p-dioxin (TCDD), phenothiazine, chlorpromazine, isosafole, γ-chlordane, allylisopropylacetamide (AIA), trans-stilbene oxide, kepone, acetone, isoniazid, pyridine, pyrazole, 4-methylpyrazole, pregnenolone 16α-carbonitrile (PCN), troleandomycin (TAO), clotrimazole, clofibrate, clobuzarit, di(2-ethylhexyl)phthalate (DEHP), or mono-(2-ethylhexyl) phthalate (MEHP). It should be noted that the aforementioned terms in parentheticals are abbreviations known in the art for the chemical names that precede them. The most preferred induction agents of the group are: beta-naphthoflavone, phenobarbital, and 3-methylcholanthrene. In the most preferred method, the induction agents are administered to a donor by injection to the intraperitoneal area. It should be noted that dosages recited herein are in terms of milligrams of induction agent per kilogram of donor bodyweight. Phenobarbital is administered preferably up to about 125 mg/kg, more preferably between about 40 to about 80 mg/kg. Beta-naphthoflavone is administered preferably up to about 180 mg/kg, more preferably between about 10 to about 15 mg/kg. 3-methylcholanthrene is preferably administered up to about 25 mg/kg, more preferably between about 5 to about 10 mg/kg. Some chemicals that are either functionally or structurally similar to those listed may be identified by one of skill in the art for practicing the invention. While not wishing to be bound by theory, many of the chemicals listed are customarily classified together in the same chemical classes with a number of other aromatic or barbituate compounds and are able to upregulate functional metabolic activity of hepatocytes. Carrier agents, adjunct agents, encapsulation means, or a combination thereof may also be added with the induction agent in the dose to regulate uptake and absorption rates of induction agent. Carriers may be aqueous, such as water or saline, and may be buffered with phosphate, borate, or citrate, for example. Non-aqueous carriers may also be used, such as dimethylsulfoxide (DMSO) or benzene. The induction agent may also be released from an encapsulation means.

One or more induction agents may be used in vivo to upregulate the enzymatic activity of the hepatocytes prior to isolation. A single induction agent may be administered to a donor one or more times prior to isolation. Induction agents may be combined, meaning as a mixture or 'cocktail' at the same time, or serially, meaning separately at different times, when administered to upregulate a profile of target enzymes. The amount of induction agent contained in the dose should be enough to induce the hepatocytes to increase their functional metabolic activity but not so much as to be lethal to the liver organ or to the donor. The time that the induction agent is provided to a donor should be long enough to result in upregulation of enzymatic detoxification activity, preferably at least about 24 hours prior isolation.

In vivo induction initiates upregulation of several functional detoxification enzymes such as cytochrome P450 isozymes and conjugating enzymes so that the hepatocytes, after isolation and incorporation in a bioreactor, sustain measurable detoxification activity for about a week. Non-induced hepatocyte cultures are not upregulated to the levels of activity found in in vivo induced hepatocyte cultures and do not sustain such levels for as long, only about 3 or 4 days.

To date, much of the cytochrome P450 isozyme work has been performed on either rat or human hepatocytes and therefore many of the known cytochrome P450 isozymes have been identified and named based on the correlation between the induction agents and the isozymes they upregulate. Extending that knowledge to porcine hepatocytes, however, one will find both similarities and differences between the induction agent and isozyme activity. The induction agents have effect on the expected isozyme or its species-specific homolog. In the preferred embodiment, hepatocytes are isolated from porcine liver so the induction agent or agents used will have effect on the expected isozyme or its porcine homolog.

Table 1 summarizes the induction activity of the most preferred induction agents for use in the invention along with their target isozymes, and the substrates that the isozymes convert. Induced hepatocytes initially express increased P450 isozyme activity on alkoxyresorufin substrates, converting them to resorufin, at a level higher than that of noninduced hepatocytes. A preferred level of targeted P450 isozyme activity increase of in vivo induced hepatocytes over non-induced hepatocytes is at least about two (2)-fold for use in the bioreactor of the invention. Certain induction agents are chosen to target and upregulate particular isozymes responsible for conversion of alkoxyresorufin substrates that may concomitantly upregulate conversion activity on other substrates. This upregulation may occur by the same or different pathways.

In the cytochrome P450 pathway, in vivo induction of a donor using phenobarbital upregulates CYPIIB1 and CYPIIB2 isozymatic activity of hepatocytes, or the activity of their porcine homologs, on benzyloxyresorufin (BROD) and pentoxyresorufin (PROD) substrates, respectively. Beta-naphthoflavone is specific for upregulation of CYPIA2 and CYPIA1 isozymatic activity, or the activity of their porcine homologs, on methoxyresorufin (MROD) and ethoxyresorufin (EROD) substrates, respectively. Methylcholanthrene upregulates CYPIIB1 isozymatic activity, or its porcine homolog, to PROD; CYPIA2 isozymatic activity, or its porcine homolog, on MROD; and CYPIA1 isozymatic activity, or its porcine homolog, on EROD. Another widely used substrate to assess hepatic enzymatic activity is 7-ethoxycoumarin (7-EC). This substrate is O-deethylated to yield a fluorescent product and is also indicative of oxidative metabolism of the cytochrome P450 enzymes. The results from these assays suggest that increases in isozymatic function are obtained following in vivo induction. Furthermore, HPLC analysis of the detoxification processes in the liver show that drugs, such as lidocaine and diazepam, which are metabolized in the liver, are cleared at a much greater rate than in the noninduced state. This finding is clinically significant as drug overdoses are a major cause of hepatic failure.

TABLE 1

Summary of Induction Activity Conferred on Alkoxyresorufin Substrates by Hepatocytes Induced In Vivo

| Induction agent | Substrates | Target Isozyme or Porcine Homolog Thereto | Degree of isozyme activity increase over noninduced control |
|---|---|---|---|
| Phenobarbital | BROD | CYPIIB2 | 20 to 100-fold |
| (40 to 80 mg/kg) | PROD | CYPIIB1 | 2 to 40-fold |
| | 7-EC | CYPIA2 | 20 to 50-fold |
| | Lidocaine | CYPIA2 | 10 to 20-fold |
| | Diazepam | CYPIIB1 | 20 to 50-fold |
| Beta-Naphthoflavone | MROD | CYPIA2 | 2 to 10-fold |
| (10 to 15 mg/kg) | EROD | CYPIA1 | 2 to 10-fold |
| 3-Methylcholanthrene | PROD | CYPIIB1 | 2 to 10-fold |
| (10 to 15 mg/kg) | MROD | CYPIA2 | 2 to 10-fold |
| | EROD | CYPIA1 | 10 to 20-fold |
| | Diazepam | CYPIIB1 | 2 to 10-fold |

The conjugation reaction pathway is another induction pathway for increased conversion activity by hepatocytes. There are several known conjugation reactions that may be upregulated by in vivo induction methods, such as the glucoronidation and sulfation conjugation reaction pathways. Glucuronidation is a primary mechanism for producing polar metabolites of xenobiotics for excretion. Phenobarbital is involved with not only cytochrome P450 isozyme activity but also conjugation enzymes. Alcohol, phenol, N-hydroxylamine, and carboxyl groups undergo O-glucoronidation; alkylamine, arylamine, amide, sulfonamide, and tertiary amine groups undergo N-glucoronidation; sulfhydryl groups undergo S-glucoronidation; and tetrahydrocannabinol groups undergo C-glucoronidation. Enzymatic glucuronidation is accomplished by the enzyme UDP-glucuronyltransferase. Another conjugation pathway for the reduction of foreign compounds and drugs bearing a hydroxyl group is sulfation. The class of sulfotransferase enzymes that may be upregulated by in vivo induction include alcohol sulfotransferase, amine N-sulfotransferase, and phenol sulfotransferase.

If a recipient patient is in need of liver assist treatment for an indication where the expression of detoxification enzyme activity is low, a liver assist device may be prepared using a mixture of cell isolates having a profile of hepatocytes with a number of enzyme activities upregulated to achieve the greatest range of detoxification activity and provide a tailor-made culture for treatment of acute failure.

After the induction stage, the cells are isolated using a modification of the Seglen method as described in Seglen, P O. *Preparation of isolated rat liver cells*. In *Methods in Cell Biology* (D M Prescott, ed.) vol. 13. Academic Press (NY, N.Y.), 1976, incorporated herein. The animal is anesthetized, opened, and the exposed liver is cannulated and perfused in situ with cold lactated Ringers solution before excision to rinse blood and excess induction agent from the liver tissue. The excised liver is transported to a biological safety cabinet where the remainder of the procedure may be performed under aseptic conditions. The extracellular matrix that provides the physical structure of the liver is then digested by quickly perfusing the organ with warmed EDTA, preferably at 37° C., followed by perfusion of 1 mg/ml collagenase at 37° C. until digestion appears complete (mean digestion time is about 22 minutes). Further digestion is then stopped with the addition of cold Hank's Balanced Salt Solution (HBSS) supplemented with calf serum. Digestion of liver matrix releases cells and cell aggregates from the matrix structure to create a suspension of cells. Undigested tissue and gallbladder are excised and the remainder of the tissue is passed through 200 micron and 100 micron stainless steel sieves to release cells and cell aggregates. The cell suspension is washed twice by centrifugation and decanting of rinse media and the cell pellet resuspended in media preferably after the third rinse. At this point, cells may be cultured in culture medium or cryopreserved in a cryopreservation medium for long-term storage for future use.

The cells are cultured as a cell suspension or plated on a surface suitable for animal cell or tissue culture, such as a culture dish, flask, or roller-bottle, which allows for hepatocyte culture and maintenance. The cells may be incorporated in a bioreactor, either in suspension or plated on a culture substrate such as a culture bead or fiber, or on a flat surface or membrane. Suitable cell growth substrates on which the cells can be grown can be any biologically compatible material to which the cells can adhere and provide an anchoring means for the cell-matrix construct to form. Materials such as glass; stainless steel; polymers, including polycarbonate, polystyrene, polyvinyl chloride, polyvinylidene, polydimethylsiloxane, fluoropolymers, and fluorinated ethylene propylene; and silicon substrates, including fused silica, polysilicon, or silicon crystals may be used as a cell growth surfaces. To enhance cell attachment or function, or both, the cell growth surface material may be chemically treated or modified, electrostatically charged, or coated with biologicals such as with extracellular matrix components or peptides. In one embodiment, the hepatocytes are cultured either within or on the surface of extracellular matrix disposed on the culture surface such as collagen in the form of a coating or a gel. In another embodiment, the hepatocytes are cultured on either a liquid-permeable membrane or a gas-permeable membrane. Other cells present in liver may also be included with the induced hepatocytes such as endothelial cells; Kupfer cells, a specialized macrophage-like cell; and, fibroblasts. A co-culture of hepatocytes with one or more of these or other types of cells may be desirable to optimize hepatocyte functioning.

The in vivo induced hepatocytes are preferably seeded in a bioreactor that is used as, or is incorporated into a LAD. Some LAD designs are based on a hollow fiber cartridge design where the hepatocytes are seeded either in the lumen of the hollow fibers or on the outside of the hollow fibers. The hollow fiber serves as a culture substrate that allows for liquid or gas transport across the hollow fiber. Other LAD designs incorporate a flat planar culture substrate. Hepatocyte culture between two collagen gel layers is described in U.S. Pat. Nos. 5,602,026, and 5,942,436 to Dunn, et al. Another design using a planar culture substrate is disclosed in U.S. Pat. No. 5,658,797 and in International PCT Publication No. WO 96/34087 to Bader, et al. Some flat planar substrates may be micropatterned so that two or more cell types may be cultured together, as a co-culture, in discrete regions on a substrate such as those described by Bhatia, et al. The disclosures of these aforementioned patents that disclose culture substrates and methods and their use as a bioreactor device to treat patients in need of liver assist are incorporated herein by reference. A preferred bioreactor design for the culture of hepatocytes incorporates a gas-permeable, liquid impermeable membrane that defines two regions of a bioreactor chamber. Hepatocytes are seeded on the surface of the membrane cultured in a liquid medium while engaging in oxygenation and other gas transfer not only in the culture medium but also across the membrane. In alternative embodiments, the membrane is treated to improve cell adhesion such as by modifying the electrical charge of the membrane, as by corona discharge, or by treating or coating the membrane with extracellular matrix components, peptides, cell-adhesion molecules or other chemicals. A preferred coating for the membrane is collagen.

When cultured, the cells are preferably contacted with a cell culture medium for a time to maintain their metabolic activity and optimal hepatocyte function. Albeit in varying concentrations, cell culture media provide a basic nutrient source for cells in the form of glucose, amino acids, vitamins, and inorganic ions, together with other basic media components. Culture media generally comprises a nutrient base further supplemented with one or more additional components such as amino acids, growth factors, hormones, anti-bacterial agents and anti-fungal agents. One preferred medium for use in the method after hepatocyte isolation comprises: Williams' E medium, newborn calf serum (NBCS), glucose, insulin, glucagon, hydrocortisone, HEPES, epidermal growth factor (EGF), and glutamine. In a more preferred embodiment, the culture medium comprises: Williams' E media supplemented with up to 1% newborn calf serum (NBCS), 4.5 g/l glucose, 0.5 U/ml insulin, 7 ng/ml glucagon, 7.5 µg/ml hydrocortisone, 10 mM HEPES, 20 ng/ml EGF, and 200 mM glutamine. Other concentrations for the aforementioned medium components or their functional equivalents may be determined for use by one of skill in the art of hepatocyte culture.

In an alternate preferred embodiment, hepatocytes are cryopreserved for storage after isolation until needed for incorporation in a bioreactor. Cryopreservation of cell suspensions, cell monolayers, and engineered tissue constructs are known in the art of cryopreservation. Cryopreservation is useful for long term storage, banking, and shipping. When needed, the cultures are removed from frozen storage, thawed, rinsed of cryopreservative, and ready for use.

After either isolation or removal from cryopreservation storage, the in vivo induced hepatocytes are preferably incorporated and cultured in a bioreactor. Hepatocytes from a single isolation induced with either a single or multiple doses of the same induction agent, or a number of induction agents, may be used. In one alternative embodiment, hepatocytes isolated from a non-induced donor are cultured in a bioreactor with hepatocytes isolated from an in vivo induced donor. In another alternative embodiment, hepatocytes from two or more donor isolations induced by the same induction agent or at least two different induction agents are combined together in the same bioreactor. If the bioreactor has multiple culture chambers or regions, hepatocytes from different donors that have been pre-treated with different induction agents may be segregated but used together for the overall functioning of the bioreactor. Combining in vivo induced hepatocyte cultures that have different enzyme activity profiles in a bioreactor used as a LAD will benefit a patient treated with the cultures in the bioreactor. In one embodiment, the bioreactor may contain several isolations of different in vivo induced hepatocyte cultures to provide the patient with a full profile of upregulated enzymes to achieve the greatest range of detoxification activity. An alternative embodiment is one where the patient may be treated with a bioreactor seeded with one or more isolations of in vivo induced hepatocytes with certain selected enzymatic activities that augment or replace certain levels of enzymatic activity where the patient's liver expresses low levels of a certain detoxification enzyme.

The bioreactor may be used to culture the cells to produce cell products or to functionally act on substances, such as toxins normally metabolized by liver. The bioreactor may serve as, or be an integral part of, a liver assist device to treat a patient in need of liver assist. Hepatocytes having upregulated enzymatic activity may be used in various types of bioreactors used as liver assist devices. Bioreactors suited for this purpose comprise suspension means, hollow fibers, radial flow surfaces and planar substrates as cell culture.

Hepatocytes that have been induced in vivo are useful to treat a patient in need of liver assist when cultured in a bioreactor that is used as, or is incorporated into, a liver assist device. Usually, hepatocyte perfusion medium and the patient's plasma or blood are circulated through the device in separate flow loops. The flow loops contact each other via a membrane for the exchange of gases, toxins, and albumin but also provide an immunological barrier between the hepatocytes and the patient.

The following examples are provided to better explain the practice of the present invention and should not be interpreted in any way to limit the scope of the present invention. Those skilled in the art will recognize that various modifications can be made to the methods described herein while not departing from the spirit and scope of the present invention.

EXAMPLES

Example 1

In Vivo Induction and Isolation of Hepatocytes

A series of in vivo induction studies utilized various doses and injection regimes ranging from 40 to 80 mg/kg on days −4 to −1 with phenobarbital in PBS; 3-methylcholanthrene (in DMSO or benzene);or, β-naphthoflavone (in DMSO) given at 5 to 15 mg/kg on days −3, −2 and/or −1 prior to surgical removal of the liver. A summary of various trials is presented in Table 2. Yorkshire/Hampshire crossbred pigs weighing 8.3±3.0 kg were obtained from E M Parsons (Hadley, Mass.). All injections of induction agents were administered into the peritoneal cavity.

TABLE 2

In vivo Induction Agents, Dosages, and Frequency

| Trial | Induction agent/ Carrier agent | Dosage (per kg donor bodyweight) | Dosing frequency (days prior to liver procurement) |
| --- | --- | --- | --- |
| Trial 1 | Phenobarbital/PBS | 80 mg/kg | Days −3 and −2 |
| Trial 2 | Phenobarbital/PBS | 40 mg/kg | Days −3, −2 and −1 |
| Trial 3 | Phenobarbital/PBS and β-Naphthoflavone/ DMSO | 40 mg/kg 10 mg/kg | Days −3, −2 and −1 Days −3, −2 and −1 |
| Trial 4 | Phenobarbital/PBS and β-Naphthoflavone/ DMSO | 40 mg/kg 10 mg/kg | Days −4, −3 and −2 Days −4, −3 and −2 |
| Trial 5 | 3-methlycholanthrene/ DMSO | 5 mg/kg | Days −3, −2 and −1 |
| Trial 6 | 3-methlycholanthrene/ benzene | 10 mg/kg | Days −3, −2 and −1 |
| Trial 7 | 3-methlycholanthrene/ benzene | 10 mg/kg | Day −1 only |

TABLE 2-continued

In vivo Induction Agents, Dosages, and Frequency

| Trial | Induction agent/ Carrier agent | Dosage (per kg donor bodyweight) | Dosing frequency (days prior to liver procurement) |
|---|---|---|---|
| Trial 8 | β-Naphthoflavone/ DMSO | 15 mg/kg | Day −1 only |

Heparin (Elkins-Sinn, Cherry Hill, N.J.) was administered intravenously at 0.5 mg/kg and donors were anesthetized with a mixture of Telazol (7–10 mg/kg, Fort Dodge Laboratories, Fort Dodge, Iowa) and Rompun (5 mg/kg, Miles, Inc., Shawnee Mission, Kans.). Plane of anesthesia was maintained with isoflurane gas and all procedures were performed in compliance with ACUC guidelines.

Cells were isolated using a modification of the Seglen method which has been described earlier (Seglen, P., *Preparation of isolated rat liver cells*, in *Meth. in Cell. Bio.* (D M Prescott, ed.), vol. 13. Academic Press (NY, N.Y.), 1976.). Briefly, the exposed liver was cannulated and perfused in situ with cold Lactated Ringers (Baxter, Deerfield, Ill.) at 250 ml/minute before excision and transport to the lab. The liver was quickly warmed and perfused with 0.2% EDTA at 37° C. This was followed by perfusion of 1 mg/ml collagenase (Life Technologies, Grand Island, N.Y.) at 37° C. until digestion appeared complete (mean digestion 22±4 min). Further digestion was stopped with the addition of cold HBSS (BioWhittaker, Walkersville, Md.) supplemented with 10% NBCS (Hyclone, Logan, Utah). Undigested tissue and gall bladder were excised and the remainder of the tissue passed through 200 and 100 micron stainless steel sieves (Fisher Scientific, Pittsburgh, Pa.). The cell suspension was washed twice and the cell pellet resuspended in culture media. Viability was determined by Trypan blue exclusion and Calcein AM staining (Molecular Probes, Eugene, Oreg.). Hepatocytes derived from the isolation process following in vivo induction show lower viability when compared to control conditions (77% n=7 versus 89% n=40), yet the cells detoxify xenobiotics at a greater rate. Immediately after isolation, $10^6$ cells were assayed for total protein with the BCA kit (Pierce Biochemical, Rockford, Ill.).

Cells were plated onto 60 mm tissue culture dishes at a density of $2\times10^6$ cells per dish (Coming, Corning, N.Y.) in Williams' E media supplemented with 1% NBCS (newborn calf serum), 4.5 g/L glucose, 0.5 U/ml bovine insulin, 7 ng/ml glucagon, 7.5 µg/ml hydrocortisone, 10 mM HEPES (Sigma), 20 ng/ml EGF, 200 mM glutamine (Life Technologies), 10 IU/ml penicillin and 10 µg/ml streptomycin (BioWhittaker). Hepatocytes were incubated at 37° C. in humidified 10% $CO_2$. Culture medium was changed on day 1 post-isolation and then every 2–3 days. Media samples taken at each change were stored for assay of albumin and urea.

For comparison, in vitro induced hepatocyte cultures were prepared. Hepatocytes were procured using the method described above but from non-induced pigs and then induced in culture. Cells were plated onto 60 mm tissue culture dishes (Corning, Corning, N.Y.) in Williams' E media supplemented with 1% NBCS (newborn calf serum), 4.5 g/L glucose, 0.5 U/ml bovine insulin, 7 ng/ml glucagon, 7.5 µg/ml hydrocortisone, 10 mM HEPES (Sigma), 20 ng/ml EGF, 200 mM glutamine (Life Technologies), 10 IU/ml penicillin and 10 µg/ml streptomycin (BioWhittaker). Experimental conditions were treated with culture medium containing any one of the following: 2 mM phenobarbital (PB; Sigma) for 96 hours, 50 µM β-naphthoflavone (BNF; Sigma) for 24 hours, or 5 µM 3-methlycholanthrene (3-MC; Sigma) for 24 hours.

Example 2

Cytochrome P450 Function Measured in Hepatocytes

The dealkylation of phenoxazone substrates has provided a powerful tool for investigating cytochrome P450 activities and isozyme profiles. Specifically, the dealkylation of the phenoxazone ethers ethoxyresorufin (EROD), methoxyresorufin (MROD), benzyloxyresorufin (BROD) and pentoxyresorufin (PROD) have allowed researchers to study the effects of induction agents on individual isozymes, namely, CYPIA1, CYPIA2, CYPIIB1 and CYPIIB2, respectively.

To measure increased isozyme activity in both in vivo and in vitro induced cultures compared to non-induced controls, both in vivo induced and in vitro induced cultures from Example 1 were incubated with EROD, MROD, PROD or BROD (Molecular Probes) at 5 µM (in Williams' E media without serum and phenol red). Dicumarol (80 µM, Sigma) was included in the incubation to limit cytosolic degradation of the resorufin end product. Samples were analyzed in a Turner 450 fluorometer at $540_{ex}$ and $585_{em}$ nm. Resorufin formation was quantified using a standard curve that was linear from 0.5 to 130 nM and data are expressed as net resorufin gain over background fluorescence. In this assay, conversion of the alkoxyresorufins to resorufin corresponds to an increase in fluorescence such that the ratio of fluorescences, or activity, corresponds directly to the level of P450 activity of a particular set of isoenzymes.

Figure 1A:
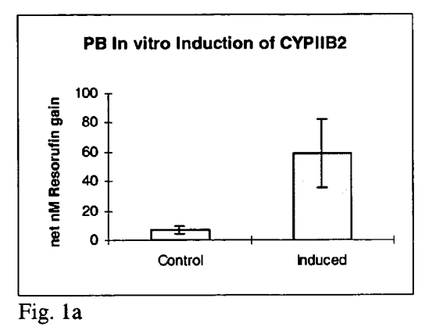
Figure 1B:
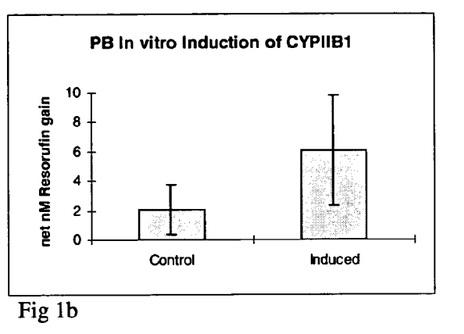
Figure 1C:
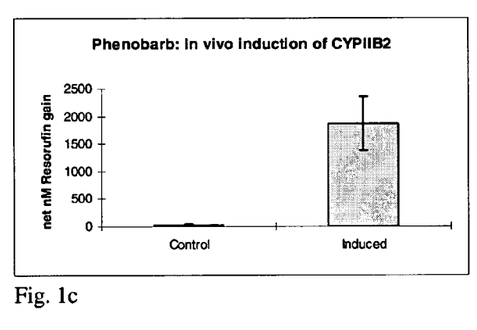
Figure 1D:
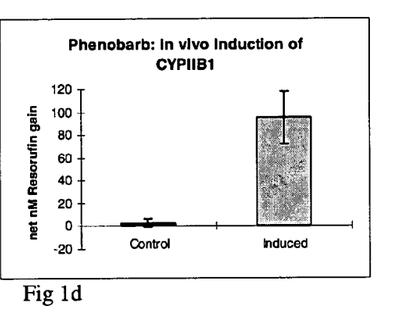

Phenobarbital induction led to increased expression of porcine CYPIIB1 and CYPIIB2 in both in vitro and in vivo induced hepatocyte cultures, however, the level of cytochrome P450 isozyme activity of in vivo induced cultures was much greater. In FIG. 1, the effects of phenobarbital (referred to as "phenobarb" and "PB" in the Figure) on in vitro and in vivo induced hepatocytes are graphically presented. In FIGS. 1a and 1b, the effect of phenobarbital was observed on cytochromes CYPIIB1 and CYPIIB2. Two million hepatocytes, which were exposed to phenobarbital for 96 hours in vitro, were incubated with the substrates for 3 hours and media samples collected for analysis of fluorescence. CYPIIB2 shows an 8.4-fold increase in function over noninduced controls following 96 hours after in vitro induction. At this point in culture, the noninduced cells show a low level of function typically seen on day 4 of culture. CYPIIB1 isozyme metabolizes PROD at a 3-fold higher rate following phenobarbital treatment. This lower level of induction with CYPIIB1 isozyme observed in porcine hepatocytes is also seen with the rat model where CYPIIB2 shows a greater level of inducibility (typically, 20–30-fold versus 5 to 10-fold (Thomas, P. E., Reik, L. M., Ryan, D. E., and Levin, W., 1983, *Induction of two immunochemically related rat liver cytochrome P-450 isozymes, cytochromes P-450c and P-450d, by structurally diverse xenobiotics*, J Biol Chem 258:4590–4598.). The impact of three daily injections, in vivo, of phenobarbital to the donor prior to that harvest of the liver is seen in FIGS. 1c and 1d. A dramatic increase in CYPIIB2 and CYPIIB1 was observed in vivo, substantially larger than what was seen in the in vitro induction effect. A 70-fold increase in function was obtained following in vivo induction for CYPIIB2, while a 38-fold upregulation is recorded with CYPIIB1. These data were collected on day one of culture from the standard plating density of 2×10⁶ on the 60 mm TC dish. The rate of resorufin formation from the BROD substrate was approximately 10.4 nM resorufin per minute from the in vivo induction (day 1). This compared favorably with the in vitro induction rate of about 0.33 nM resorufin formed per minute (day 4), 69-times higher than the average control rate of resorufin formed on day 1 from BROD at 0.15 nM per minute.

Figure 2A:
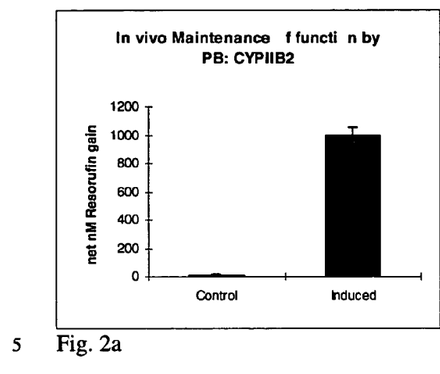
FIG. 2 shows maintenance of function of CYPIIB2 and CYPIIB1 isozymes at four days after plating of hepatocytes induced with phenobarbital (PB) in vivo and in vitro.
Figure 2B:
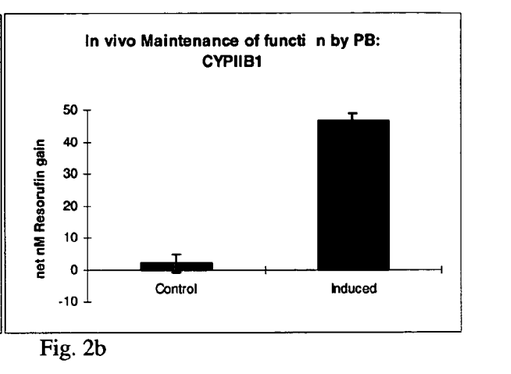
Figure 3A:
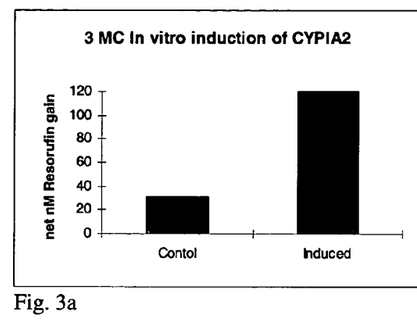
Figure 3B:
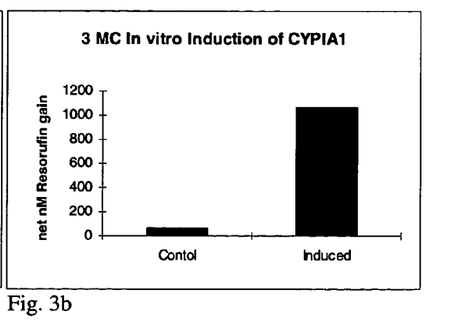
Figure 3C:
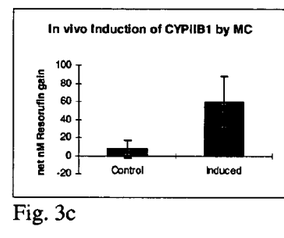
FIGS. 3c, d, and e demonstrate the impact that 3-methylcholanthrene possessed in vivo for CYPIIB1 (PROD), CYPIA2 (MROD), and CYPIA1 (EROD), respectively.
Figure 3D:
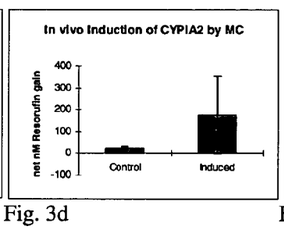
Figure 3E:
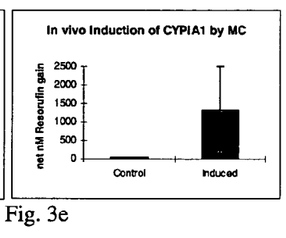

In vivo induction with phenobarbital also demonstrated maintenance of hepatocyte function in induced hepatocyte cultures longer than non-induced cultures. FIG. 2 shows the measurable enzyme activity at four days after plating of hepatocytes induced in vivo with 40 to 80 milligrams of phenobarbital/PBS per kilogram donor bodyweight once each day, 96 hours (4 doses) prior to liver harvest. Four days after plating, the cytochrome P450 activity of in vivo-induced hepatocytes was reduced by about 50% but were still highly active compared to noninduced controls.

β-Naphthoflavone, both in vitro and in vivo, upregulates CYPIA1 in porcine hepatocytes. In vitro induction of porcine CYPIA1 (EROD Substrate) following 24 hours of induction in media containing 50 μM β-Naphthoflavone ("BNF") caused a 14.8-fold increase in function over control metabolic conversion of EROD. The in vitro induction increases the resorufin formed per minute from control levels of 0.27 nM to 4.0 nM.

FIG. 3 depicts the effects of 3-methlycholanthrene ("3 MC" or "MC") on both in vitro and in vivo induced hepatocyte cultures. In vitro induction of CYPIA2 (MROD), FIG. 3a, and CYPIA1 (EROD), FIG. 3b, is shown. Porcine hepatocytes were cultured in media containing 5 μM 3-methylcholanthrene for 24 hours. Both CYPIA1 and CYPIA2 were affected, increasing their conversion rates to 18-fold and 4-fold that of the control rates, respectively. These data were also for two million hepatocytes on day 2 of culture. In vivo induction of CYPIIB1 (PROD), FIG. 3c, CYPIA2 (MROD), FIG. 3d, and CYPIA1 (EROD), FIG. 3e, by 3-methylcholanthrene are also shown. FIGS. 3c, d, and e demonstrate the wider range of impact that 3-methylcholanthrene possessed in vivo. CYPIA1 and CYPIA2 were affected by 3-methylcholanthrene, 24-fold and 7.6-fold over noninduced controls, respectively. An 8.4-fold upregulation of CYPIIB1 (PROD) was measured following in vivo administration of the induction agent. This effect on CYPIIB1 was not observed following the in vitro induction with the same induction agent.

Example 3

Lidocaine and Diazepam Clearance

Lidocaine (Paddock Laboratories Inc., Minneapolis, Minn.) clearance was assayed using a modification of the protocol of Nyberg et al. *Pharmacokinetic analysis verifies P450 function in in vitro and in vivo application of a bioartificial liver*, ASAIO, 39:M252–M256, 1993. Lidocaine (740 μM) was added to the control, and both in vivo induced and in vitro induced cultures of Example 1 for the indicated times; media samples were then collected and frozen until extraction. Solid phase extraction was performed with Oasis cartridges (Waters Corp., Milford, Mass.) and a Waters extraction manifold as follows: Cartridges were primed with 99% MeOH 1% HCl and 0.5 M Borax. The sample was loaded onto the column, washed with 0.5 M Borax, eluted with MeOH/HCl and then evaporated and reconstituted with 250 μl of mobile phase (85% 50 mM NH₄HPO₄+10 mM Hexanesulfonic Acid, pH 3.0, 15% Acetonitrile). The reverse phase HPLC was carried out with a flow rate of 1 ml/minute on a Microsorb C8 column (Rainin Instrument Co., Woburn, Mass.) at room temperature and monitored at 214 nm. Lidocaine eluted at approximately 37 minutes; MEGX, the major metabolite, eluted at 27 minutes. In this assay, high percentages of lidocaine cleared correspond to high P450 activity; the higher these percentages, the greater the P450 activity.

Diazepam clearance was assayed in the cultures of Example 1 using a method similar to that of Jauregui et al. *Xenobiotic induction of P-450 PB-4 (IIB1) and P-450c (IA1) and associated monooxygenase activities in primary cultures of adult rat hepatocytes*. Xeno, 21(9):1091–106. 1991. After addition of 70 μM diazepam (Sigma) for 48 hours, media samples were collected and frozen until assay. Oasis solid phase extraction was performed on each sample with a priming step of 100% MeOH, followed by RODI. Samples were loaded onto the column and washed with 5% MeOH in RODI. Elution off the column was achieved with 100% MeOH. As with lidocaine, the samples were evaporated and reconstituted with mobile phase (65% MeOH, 35% 0.01M Ammonium Acetate, pH 6.0). This reverse phase HPLC run was conducted at a flow rate of 1.0 ml/min through a micro-Bondpak C18 column (Waters) with absorbance set at 254 nm. The temperature was held constant at 24.5° C. Diazepam eluted at approximately 11 minutes, with metabolites nordiazepam, temazepam and oxazepam eluting at 10, 8, and 7 minutes, respectively. In this assay, high percentages of initial diazepam cleared and converted to nordiazepam and temazepam correspond to high P450 activity. Similarly, high percentages of lidocaine cleared correspond to high P450 activity. The higher these percentages, the greater the P450 activity.

Results showed that phenobarbital induction can upregulate CYPIIB1 in the resorufin assay (PROD) (see Example 2) and here, similarly increased diazepam clearance rates. This assay, in particular, may be most clinically significant as it has been postulated that benzodiazepine-like compounds are implicated in human hepatic encephalopathy (Jones, E. A., Gammel, S. H., Basile, A. S., Mullen, K. D., Bassett, M. L. Schaffer, D. F., and Skolnick, P., 1989, *Hepatic encephalopathy and benzodiazepine receptor ligands*, in *Hepatic Encephalopathy: Pathophysiology and Treatment*, ed. by R. F. Butterworth and G. P. Layrargues (Clifton: Humana Press), pp. 273–286).

Lidocaine clearance showed an upregulation following in vivo phenobarbital induction to about 10 to 20-fold over non-induced control cultures. Diazepam clearance showed an upregulation following in vivo induction by 3-methlycholanthrene to about 2 to 10-fold over non-induced control cultures.

Example 4

7-Ethoxycoumarin Metabolism

7-Ethoxycoumarin (7EC, Sigma) metabolism was measured by incubating cells (control and both in vivo induced and in vitro induced cells) of Example 1 at 37° C. with 375 μg/ml of 7-ethoxycoumarin in phenol red free culture media for the indicated time. Samples were then analyzed for the fluorescent product using a Turner 450 fluorometer with halogen illumination at $360_{ex}$ and $415_{em}$.

Figure 4:
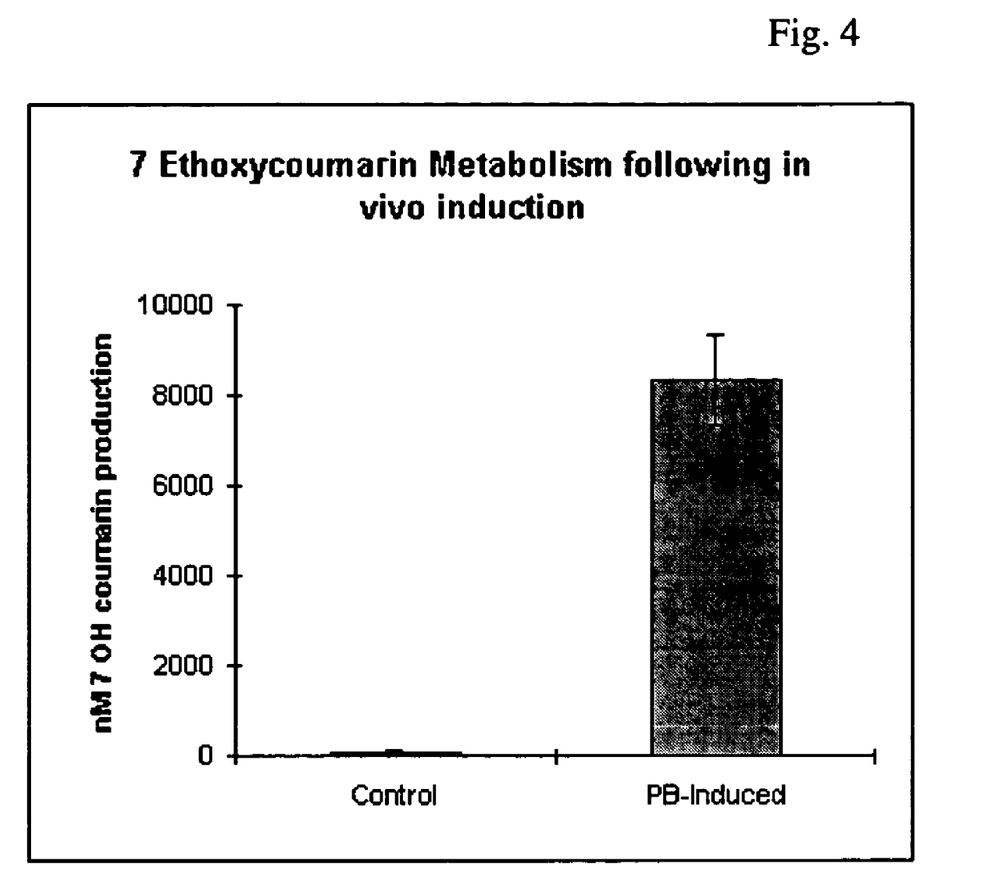
FIG. 4 shows that 7-ethoxycoumarin O-deethylation is higher when hepatocytes are induced in vivo with phenobarbital than noninduced control cultures.

7-Ethoxycoumarin O-deethylation is also higher following induction with phenobarbital. The impact of in vivo phenobarbital administration is observed on 7-ethoxycoumarin metabolism, as shown in FIG. 4. In this experiment, 24 hours after adding the 7-ethoxycoumarin substrate, the induced hepatocytes showed a dramatic production of 7-OH coumarin (umbelliferone), the major metabolite of 7-ethoxycoumarin. The induction increased umbelliferone production rates from 2.58±1.9 nM per hour to 346±41.4 nM per hour.

Example 5

Albumin and Transferrin Measurement

Albumin secretion was measured using a standard competitive ELISA format. Maxisorp Microtiter plates (Nunc) were coated overnight with 200 µg/ml porcine albumin (Accurate Chemical, Westbury, N.Y.). Following a wash step with Tween 20 (Pierce, Rockford, Ill.), 50 µl of sample or standard (Accurate) was incubated with a HRP (horseradish peroxidase)-conjugated goat anti-pig albumin antibody (Bethyl Labs, Montgomery, Tex.) for 90 minutes. Color was produced by addition of OPD substrate (Pierce) and the reaction was stopped by adding $H_2SO_4$. Plates were read at 490 nm using SoftMax Pro software and to a SpectraMax 250 plate reader (Molecular Devices).

Transferrin was similarly assessed using Maxisorp plates coated overnight with 100 µg/ml swine transferrin (Accurate). Following a wash with Tween 20/PBS, 50 µl of sample or standard was incubated with HRP-conjugated rat anti-swine transferrin (Accurate) for 90 minutes. Color development was produced, stopped and analyzed as above.

Synthetic functions of the hepatocytes, namely albumin and transferrin production were maintained, indicating that the induction treatment did not downregulate these synthetic functions in isolated porcine hepatocytes.

Example 6

Hepatocellular Deamination of Medium Based on Synthesis of Urea

The clearance of ammonia, its salts, and aminated components in the medium, through deamination, is believed to be a critical function of hepatocytes in vivo and a desired function of these cells as part of a liver-assist device. Deamination results in the formation of urea, which in vivo is cleared by the renal system.

The synthesis of urea by in vivo induced hepatocytes were measured using a colorimetric method for the determination of nitrogen, available as Kit #640-B from Sigma Diagnostics (St. Louis, Mo.). Samples were collected periodically after seeding of cells into devices and treated with urease to hydrolyze urea to $NH_3$ and $CO_2$. The resulting $NH_3$ then was reacted with hypochlorite and phenol in the presence of the catalyst, sodium nitroprusside, to form indophenol. The optical absorbance of the resulting solution of indophenol was measured at 570 nm and converted to concentration of urea in the original sample using a standard curve. Data were expressed as amount of urea produced per device per day by multiplying the concentrations by volume of medium in the device and dividing by number of days since sampling. The synthesis of urea by in vivo induced hepatocytes was maintained indicating that the induction treatment did not downregulate this synthetic function in isolated porcine hepatocytes.

Example 7

In Vivo Induced Hepatocytes Cultured in a Bioreactor Device

To test the feasibility of in vivo induced cells for use in a new bioreactor design, incorporating new structural features and material composition, prototype bioreactor device units were compared to standard tissue culture dishes. A bioreactor device was constructed having an assembly of upper and lower housings, separated by a gas-permeable, liquid-impermeable membrane to form upper and lower chambers. The upper chamber had an access window for addition of cells and media transfer and a cover to allow aseptic transportation of the assembled device after seeding with cells and to prevent spillage or exposure of the interior of the device to contaminants. The membrane used was Polyflex® (Plastics Suppliers, Inc., Columbus, Ohio), a 0.002"-thick film of polystyrene that had been treated with a corona discharge. The upper and lower polycarbonate housings were bolted together to sandwich the membrane/frame assembly, and a gas and liquid-tight seal was formed between the housings using O-rings disposed between the housings. All assembly steps, unless otherwise noted, were conducted in a biological safety cabinet and occurred after sterilizing all parts by autoclaving or other proven treatment (e.g., gamma irradiation or exposure to an oxidizing gas such as ethylene oxide, peracetic acid, and/or hydrogen peroxide). All materials were handled with either sterile tweezers or gloves within the cabinet.

Phenobarbital in phosphate buffered saline was administered at about 40 mg per kilogram of bodyweight at 4, 3, and 2 days to a porcine donor, a Yorkshire/Hampshire crossbred pig weighing 8.3±3.0 kg, prior to surgically removing the liver and isolating the hepatocytes according to the Seglen method disclosed in Example 1.

Primary hepatocytes were suspended in complete medium (Williams E medium supplemented with 4.5 g/L glucose, 0.5 U/mL bovine insulin, 7 ng/mL glucagon, 7.5 µg/mL hydrocortisone, 10 mM HEPES, 20 ng/mL EGF, 20 mM glutamine, 10 IU penicillin, and 10 µg streptomycin) with 1% new-born calf serum (NBCS) were obtained from porcine donors with the following procedure.

Before seeding cells, the membranes of the bioreactor devices and the tissue culture dishes were pre-coated with a sterile 4 mL volume solution of 40 µg/mL Type I collagen in water for 45 minutes, followed by aspiration of this solution and rinsing with an equal volume of sterile phosphate-buffered saline (PBS), prior to seeding of cells.

A suspension of cells in medium was evenly suspended and was seeded at an initial density of $2 \times 10^6$ cells per device. The cover to the device was removed, the cell suspension pipetted onto the membrane, the device agitated carefully to distribute the liquid evenly onto the surface of the membrane, and the cover replaced. The cell-seeded devices and tissue culture dishes were transferred to an incubator at 37° C. and 85% relative humidity in 10% $CO_2$.

After approximately 18–24 hours the device was removed from the incubator, placed back in the biological safety cabinet, cover removed, and the medium aspirated using a sterile Pasteur pipette. The isozyme activity of the hepatocytes in both the tissue culture plates and the prototype device were assayed according to the methods of Example 2.

BROD conversion (CYPIIB2) and EROD conversion (CYPIA1) were similar on both the tissue culture and bioreactor device conditions. These results indicate that in vivo induced hepatocytes having upregulated enzymatic detoxification activity may be used in a bioreactor.

What is claimed is:

1. A hepatocyte cell culture comprising liver cells in a bioreactor for use in a liver assist device comprising one or more hepatocytes having increased detoxification enzyme activity,
   wherein the hepatocytes are isolated from a liver of a mammalian donor that had been administered at least one induction agent prior to isolation of the hepatocytes,
   wherein the induction agent is selected from the group consisting of: beta-naphthoflavone, phenobarbital, 3-methylcholanthrene, ethanol, dexamethasone, arochlor 1254, 2,3,7,8-tetrachlorodibenzo-p-dioxin, phenothiazine, chlorpromazine, isosafole, γ-chlordane, allylisopropylacetamide, trans-stilbene oxide, kepone, acetone, isoniazid, pyridine, pyrazole, 4-methylpyrazole, pregnenolone 16α-carbonitrile, troleandomycin, clotrimazole, clofibrate, clobuzarit, di(2-ethylhexyl)phthalate, and mono-(2-ethylhexyl)phthalate.

2. The hepatocyte cell culture of claim 1, wherein the induction agent is phenobarbital and wherein the thus induced hepatocytes have a functional cytochrome P450 isozyme activity on BROD substrates which is about 20 to about 100-fold greater than hepatocytes isolated from a mammalian donor that was not administered an induction agent.

3. The hepatocyte cell culture of claim 1, wherein the induction agent is phenobarbital and wherein the thus induced hepatocytes have a functional cytochrome P450 isozyme activity on PROD substrates which is about 2 to about 40-fold greater than hepatocytes isolated from a mammalian donor that was not administered an induction agent.

4. The hepatocyte cell culture of claim 1, wherein the induction agent is phenobarbital and wherein the thus induced hepatocytes have a functional cytochrome P450 isozyme activity on 7-ethoxycoumarin substrates which is about 20 to about 50-fold greater than hepatocytes isolated from a mammalian donor that was not administered an induction agent.

5. The hepatocyte cell culture of claim 1, wherein the induction agent is phenobarbital and wherein the thus induced hepatocytes have a functional cytochrome P450 isozyme activity on lidocaine which is about 10 to about 20-fold greater than hepatocytes isolated from a mammalian donor that was not administered an induction agent.

6. The hepatocyte cell culture of claim 1, wherein the induction agent is phenobarbital and wherein the thus induced hepatocytes have a functional cytochrome P450 isozyme activity on lidocaine which is about 20 to about 50-fold greater than hepatocytes isolated from a mammalian donor that was not administered an induction agent.

7. The hepatocyte cell culture of claim 1, wherein the induction agent is beta-naphthoflavone and wherein the thus induced hepatocytes have a functional cytochrome P450 isozyme activity on MROD substrates which is about 2 to about 10-fold greater than hepatocytes isolated from a mammalian donor that was not administered an induction agent.

8. The hepatocyte cell culture of claim 1, wherein the induction agent is beta-naphthoflavone and wherein the thus induced hepatocytes have a functional cytochrome P450 isozyme activity on EROD substrates which is about 2 to about 10-fold greater than hepatocytes isolated from a mammalian donor that was not administered an induction agent.

9. The hepatocyte cell culture of claim 1, wherein the induction agent is 3-methylcholanthrene and wherein the thus induced hepatocytes have a functional cytochrome P450 isozyme activity on PROD substrates which is about 2 to about 10-fold greater than hepatocytes isolated from a mammalian donor that was not administered an induction agent.

10. The hepatocyte cell culture of claim 1, wherein the induction agent is 3-methylcholanthrene and wherein the thus induced hepatocytes have a functional cytochrome P450 isozyme activity on MROD substrates which is about 2 to about 10-fold greater than hepatocytes isolated from a mammalian donor that was not administered an induction agent.

11. The hepatocyte cell culture of claim 1, wherein the induction agent is 3-methylcholanthrene and wherein the thus induced hepatocytes have a functional cytochrome P450 isozyme activity on EROD substrates which is about 10 to about 20-fold greater than hepatocytes isolated from a mammalian donor that was not administered an induction agent.

12. The hepatocyte cell culture of claim 1, wherein the induction agent is 3-methylcholanthrene and wherein the thus induced hepatocytes have a functional cytochrome P450 isozyme activity on diazepam substrates which is about 2 to about 10-fold greater than hepatocytes isolated from a mammalian donor that was not administered an induction agent.

13. A bioreactor comprising:
   a bioreactor chamber comprising a first region and a second region;
   a gas-permeable, liquid impermeable membrane defining said first region and said second region of said bioreactor chamber; and
   hepatocytes having increased detoxification enzyme activity,
   wherein the hepatocytes are isolated from a liver of a mammalian donor that had been administered at least one induction agent prior to isolation of hepatocytes,
   wherein the induction agent is selected from the group consisting of beta-zaphthoflavone, phenobarbiral, 3-methyicholanthrene, ethanol, dexamethasone, arochlor 1254, 2,3,7,8-tetrachlorodibenzn-p-dloxln, phenothiazine, chlorpromazine, isosafole, γ-chlordane, allylisopropylacetamide, trans-stilbene oxide, kepone, acetone, isoniazid, pyridine, pyrazole, 4-methylpzyrazole, pregnenolone 16α-carbonitrile, troleandomycin, clotrimazola, clofibrate, clobuzarit, di(2-ethylexyl)phthalate, and mono-(2-ethylhexyl)phthalate;
   wherein the bioreactor can be used in a liver assist device.

* * * * *